United States Patent
Garza et al.

(10) Patent No.: US 11,911,040 B2
(45) Date of Patent: *Feb. 27, 2024

(54) FLOW ATTENUATION DEVICE

(71) Applicant: Arissa Medical, Inc., Newark, CA (US)

(72) Inventors: Armando Garza, San Jose, CA (US); Be Thi Le, San Jose, CA (US); Tae Hee Cho, Oakland, CA (US); Regina Coeli Velasco, Fremont, CA (US)

(73) Assignee: Arissa Medical, Inc., Newark, CA (US)

(*) Notice: Subject to any disclaimer, the term of this patent is extended or adjusted under 35 U.S.C. 154(b) by 401 days.

This patent is subject to a terminal disclaimer.

(21) Appl. No.: 17/341,669

(22) Filed: Jun. 8, 2021

(65) Prior Publication Data

US 2022/0000489 A1 Jan. 6, 2022

Related U.S. Application Data

(63) Continuation of application No. 16/100,775, filed on Aug. 10, 2018, now Pat. No. 11,071,551.

(Continued)

(51) Int. Cl.
*A61B 17/12* (2006.01)
*A61F 2/90* (2013.01)
(Continued)

(52) U.S. Cl.
CPC .... *A61B 17/12154* (2013.01); *A61B 17/1214* (2013.01); *A61B 17/12113* (2013.01);
(Continued)

(58) Field of Classification Search
CPC ........ A61B 17/12022; A61B 17/12113; A61B 17/1214; A61B 17/12145; A61B 17/1215;
(Continued)

(56) References Cited

U.S. PATENT DOCUMENTS

| | | | |
|---|---|---|---|
| 5,354,295 | A | 10/1994 | Guglielmi et al. |
| 5,382,259 | A | 1/1995 | Phelps et al. |

(Continued)

FOREIGN PATENT DOCUMENTS

| | | | |
|---|---|---|---|
| CN | 101282697 A | 10/2008 |
| CN | 101340858 A | 1/2009 |

(Continued)

OTHER PUBLICATIONS

Chinese Office Action for Chinese Patent Application No. 201880053135.0 dated Nov. 28, 2022 (9 pages).

(Continued)

*Primary Examiner* — Robert A Lynch
(74) *Attorney, Agent, or Firm* — Goodwin Procter LLP

(57) ABSTRACT

An embolic device for treating aneurysms or other vascular disorders may be more compliant than conventional devices, while still achieving desired porosity. In particular, the device may achieve the desired porosity only at discrete sections along the length of the device where such a porosity is required (e.g., sections that will block the neck of the aneurysm upon deployment). The remaining sections of the device can be configured to increase the device's compliance. For example, the remaining sections can be formed from less material than the sections with the desired porosity. In some instances, the sections with the desired porosity are formed from mesh-screen segments and the remaining sections are formed from coil segments. In some instances, the mesh-screen segments are configured to further enhance the device's compliance. For example, the mesh-screen segment can be formed from a layered structure that achieves greater compliance than conventional braided structures.

20 Claims, 9 Drawing Sheets

Related U.S. Application Data

(60) Provisional application No. 62/546,809, filed on Aug. 17, 2017.

(51) Int. Cl.
| | |
|---|---|
| *A61L 31/14* | (2006.01) |
| *A61B 17/00* | (2006.01) |
| *A61B 90/00* | (2016.01) |
| *A61F 2/82* | (2013.01) |

(52) U.S. Cl.
CPC .......... *A61B 17/12168* (2013.01); *A61F 2/90* (2013.01); *A61L 31/146* (2013.01); *A61B 2017/00526* (2013.01); *A61B 2017/00867* (2013.01); *A61B 2017/12054* (2013.01); *A61B 2090/3966* (2016.02); *A61F 2002/823* (2013.01); *A61L 2400/04* (2013.01); *A61L 2400/16* (2013.01); *A61L 2430/36* (2013.01)

(58) Field of Classification Search
CPC ........ A61B 17/12154; A61B 17/12168; A61B 17/12172; A61B 17/12177; A61B 2017/00526; A61B 2017/00867; A61B 2017/1205; A61B 2017/12054; A61B 2017/12113; A61B 2017/12118; A61B 2090/3966; A61F 2/86; A61F 2/88; A61F 2/90; A61F 2002/823; A61L 2430/36; A61L 31/146; A61L 2400/04; A61L 2400/16

See application file for complete search history.

(56) References Cited

U.S. PATENT DOCUMENTS

| | | | |
|---|---|---|---|
| 5,723,004 A | 3/1998 | Dereume et al. | |
| 5,769,884 A | 6/1998 | Solovay | |
| 5,824,052 A | 10/1998 | Khosravi et al. | |
| 5,951,599 A | 9/1999 | McCrory | |
| 6,093,199 A | 7/2000 | Brown et al. | |
| 6,210,433 B1 | 4/2001 | Larre | |
| 6,228,072 B1 | 5/2001 | Omaleki et al. | |
| 6,309,367 B1 | 10/2001 | Boock | |
| 6,312,463 B1 | 11/2001 | Rourke et al. | |
| 6,346,117 B1 | 2/2002 | Greenhalgh | |
| 6,375,606 B1 | 4/2002 | Garibaldi et al. | |
| 6,428,558 B1 | 8/2002 | Jones et al. | |
| 6,589,265 B1 | 7/2003 | Palmer et al. | |
| 6,811,560 B2 | 11/2004 | Jones et al. | |
| 6,994,689 B1 | 2/2006 | Zadno-Azizi et al. | |
| 7,156,871 B2 | 1/2007 | Jones et al. | |
| 7,232,461 B2 | 6/2007 | Ramer | |
| 7,572,288 B2 | 8/2009 | Cox | |
| 7,611,530 B2 | 11/2009 | Pomeranz et al. | |
| 7,621,928 B2 | 11/2009 | Thramann et al. | |
| 7,637,942 B2 | 12/2009 | Mangiardi et al. | |
| 7,763,011 B2 | 7/2010 | Ortiz et al. | |
| 7,875,044 B2 | 1/2011 | Feller, III et al. | |
| 8,075,615 B2 | 12/2011 | Eberhardt et al. | |
| 8,425,548 B2 | 4/2013 | Connor | |
| 8,444,668 B2 | 5/2013 | Jones et al. | |
| 8,974,487 B2 | 3/2015 | Connor et al. | |
| 9,039,726 B2 | 5/2015 | Becking | |
| 9,060,777 B1 | 6/2015 | Wallace et al. | |
| 9,192,491 B1 | 11/2015 | Raju et al. | |
| 9,295,568 B2 | 3/2016 | Berez et al. | |
| 9,339,367 B2 | 5/2016 | Carpenter et al. | |
| 9,358,140 B1 | 6/2016 | Connor et al. | |
| 9,433,518 B2 | 9/2016 | Rudakov et al. | |
| 9,451,964 B2 | 9/2016 | Guo et al. | |
| 9,517,146 B2 | 12/2016 | Fierens et al. | |
| 9,561,097 B1 | 2/2017 | Kim et al. | |
| 9,675,476 B2 | 6/2017 | Berez et al. | |
| 11,071,551 B2* | 7/2021 | Garza ................... A61L 31/146 | |
| 2002/0169473 A1 | 11/2002 | Sepetka et al. | |
| 2003/0109917 A1 | 6/2003 | Rudin et al. | |
| 2003/0199887 A1 | 10/2003 | Ferrera et al. | |
| 2005/0137677 A1 | 6/2005 | Rush | |
| 2005/0283220 A1 | 12/2005 | Gobran et al. | |
| 2006/0116714 A1 | 6/2006 | Sepetka et al. | |
| 2006/0200234 A1 | 9/2006 | Hines | |
| 2006/0271098 A1 | 11/2006 | Peacock | |
| 2006/0276831 A1 | 12/2006 | Porter et al. | |
| 2007/0016283 A1 | 1/2007 | Greenhalgh et al. | |
| 2007/0021816 A1 | 1/2007 | Rudin | |
| 2007/0219619 A1 | 9/2007 | Dieck et al. | |
| 2007/0225794 A1 | 9/2007 | Thramann et al. | |
| 2007/0270902 A1 | 11/2007 | Slazas et al. | |
| 2008/0004653 A1 | 1/2008 | Sherman et al. | |
| 2008/0097508 A1 | 4/2008 | Jones et al. | |
| 2009/0043330 A1 | 2/2009 | To | |
| 2009/0270974 A1 | 10/2009 | Berez et al. | |
| 2011/0054511 A1 | 3/2011 | Henson et al. | |
| 2011/0054589 A1 | 3/2011 | Bashiri et al. | |
| 2011/0144669 A1 | 6/2011 | Becking et al. | |
| 2012/0197283 A1 | 8/2012 | Marchand et al. | |
| 2012/0253377 A1 | 10/2012 | Slazas et al. | |
| 2012/0296408 A1 | 11/2012 | Jones et al. | |
| 2013/0116722 A1 | 5/2013 | Aboytes et al. | |
| 2013/0123901 A1 | 5/2013 | Connor et al. | |
| 2013/0261730 A1 | 10/2013 | Bose et al. | |
| 2014/0114343 A1 | 4/2014 | Lee et al. | |
| 2014/0128901 A1 | 5/2014 | Kang et al. | |
| 2014/0303667 A1 | 10/2014 | Cox et al. | |
| 2014/0336741 A1 | 11/2014 | Connor et al. | |
| 2015/0173770 A1 | 6/2015 | Warner et al. | |
| 2015/0196405 A1* | 7/2015 | Rudakov ................... A61F 2/90 623/1.15 |
| 2015/0342613 A1 | 12/2015 | Aboytes et al. | |
| 2016/0022275 A1 | 1/2016 | Garza | |
| 2016/0032503 A1 | 2/2016 | Lorenzo | |
| 2016/0066918 A1 | 3/2016 | Chen | |
| 2016/0151141 A1 | 6/2016 | Zimmerman | |
| 2016/0199204 A1 | 7/2016 | Pung et al. | |
| 2016/0317158 A1 | 11/2016 | Lorenzo et al. | |
| 2017/0020532 A1 | 1/2017 | Islak et al. | |
| 2017/0079661 A1 | 3/2017 | Bardsley et al. | |

FOREIGN PATENT DOCUMENTS

| | | |
|---|---|---|
| CN | 203885667 U | 10/2014 |
| CN | 106073848 A | 11/2016 |
| CN | 106659505 A | 5/2017 |
| DE | 102010027106 A1 | 1/2012 |
| EP | 3087934 B1 | 8/2019 |
| GB | 2494820 B | 9/2013 |
| JP | 2016-209575 A | 12/2016 |
| JP | 2017-516552 A | 6/2017 |
| KR | 101300437 B1 | 8/2013 |
| WO | WO-94/09705 A1 | 5/1994 |
| WO | WO-00/07524 A1 | 2/2000 |
| WO | WO-2003020171 A3 | 12/2003 |
| WO | WO-2007/047851 A2 | 4/2007 |
| WO | WO-2007/053568 A1 | 5/2007 |
| WO | WO-2011/072053 A1 | 6/2011 |
| WO | WO-2014036809 A1 | 3/2014 |
| WO | WO-2015/184075 A1 | 12/2015 |
| WO | WO-2016/014985 A1 | 1/2016 |
| WO | WO-2017/035275 A1 | 3/2017 |
| WO | WO-2017/106265 A1 | 6/2017 |

OTHER PUBLICATIONS

European Search Report for European Patent Application No. 22193797.2, dated Nov. 24, 2022 (12 pages).

Japanese Office Action for Japanese Patent Application No. 2020-509084, dated May 30, 2022 (6 pages).

Japanese Office Action for Japanese Patent Application No. 2020-509084, dated Sep. 20, 2022 (5 pages).

Japanese Office Action for Japanese Patent Application No. 2020-509084, dated Apr. 10, 2023 (4 pages).

(56) References Cited

OTHER PUBLICATIONS

International Search Report and Written Opinion issued in International Application No. PCtT/US2018/046263, dated Oct. 31, 2018.

* cited by examiner

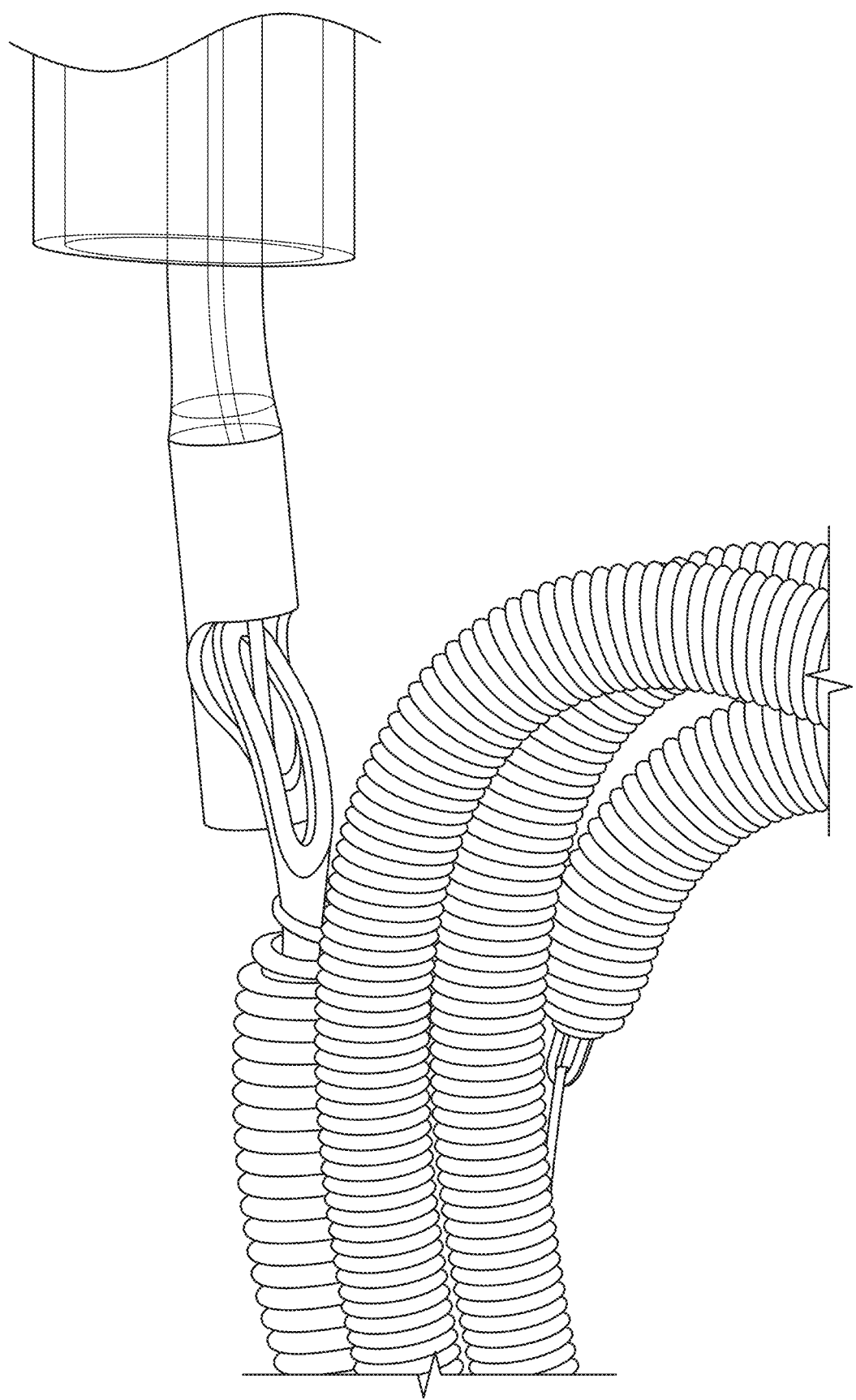

FLOW ATTENUATION DEVICE

CROSS-REFERENCE TO RELATED APPLICATION

This application is a continuation of and claims priority to and the benefit of, and incorporates herein by reference in its entirety, U.S. patent application Ser. No. 16/100,775, which was filed on Aug. 10, 2018, which claims priority to and the benefit of, and incorporates herein by reference in its entirety, U.S. Provisional Patent Application No. 62/546,809, which was filed on Aug. 17, 2017.

TECHNICAL FIELD

In general, various embodiments of this invention relate to embolic implants for use in the minimally-invasive treatment of aneurysms (e.g., sidewall, bifurcation, bilobed, wide-neck, etc.) and other vascular disorders and, more specifically, to an embolic implant that features certain discrete segments that achieve a desired porosity and other segments that increase the compliance of the device.

BACKGROUND

In general, an aneurysm is a swelling or bulge that forms a cavity in the wall of a blood vessel. One type of aneurysm is a cerebral aneurysm, which forms in an artery of the brain. A cerebral aneurysm may develop suddenly without initial symptoms, and can cause extreme pain. In general, in 15% of cerebral aneurysm cases, the patient dies suddenly upon development of the cerebral aneurysm; in another 15% of cerebral aneurysm cases, the patient dies under medical treatment; and in 30% of cerebral aneurysm cases, the patient survives after treatment but feels an acute aftereffect. As such, a cerebral aneurysm (or any aneurysm) is a very concerning development.

The treatment of aneurysms and other similar vascular disorders often involves the placement of microcoils within the cavity formed by the aneurysm or disorder. Doing so can cause blood to clot, prevent an additional inflow of blood, and decrease the risk of the aneurysm or disorder rupturing (i.e., an embolization). In order to be effective, an embolic microcoil must apply pressure sufficient to prevent additional inflow of blood, but not an excessive amount of pressure that causes rupture.

A critical parameter for most embolic devices is porosity, which is a measure of the amount of fluid that can pass through the embolic device into the aneurysm. In order to achieve a desired porosity, most conventional embolic devices are formed from braided wires or mesh structures that form pores 101 of a particular size (e.g., as shown in FIG. 1). While these structures can be effective in achieving desired porosity, the amount of material they require (e.g., numerous overlapping wires) can negatively affect the compliance of the device. Compliance (sometimes referred to as "softness") is a measure of the flexibility and conformability of the device. If an embolic device is too stiff, it can be difficult to deliver through tortuous pathways and may apply excessive pressure to the aneurysm wall, risking its rupture. Most current embolic devices give up significant compliance in order to achieve the desired porosity.

Accordingly, there is a need for an improved embolic device that achieves desired porosity without compromising significant compliance.

SUMMARY OF THE INVENTION

In various embodiments, the present invention relates to an improved embolic device that achieves a desired porosity without compromising as much compliance as conventional devices. In particular, the device leverages the fact that the desired porosity is only required at certain discrete section(s) along the length of the device (sometimes referred to herein as "porosity sections"), e.g., the section of the device that blocks the neck (or opening) of the aneurysm when the device is deployed. In this application, the term "porosity section" refers to a portion of the device having a desired porosity. In some instances, this desired porosity of the porosity section is greater than the porosity of the remaining sections of the device, but the opposite is also true in some cases. The remaining sections of the device (sometimes referred to herein as "compliance sections") need not have the desired porosity and can thus be configured to increase the device's compliance. For example, the compliance sections can be formed of less material than the porosity sections. Examples of compliance sections include sections of the device located in the middle of the aneurysm cavity or along the interior wall of the aneurysm cavity upon deployment of the device. Inclusion of the compliance sections can increase the overall compliance of the entire device and result in a device having superior compliance over current devices that unnecessarily maintain the desired porosity over their entire length.

In general, in one aspect, embodiments of the invention feature an embolic device for use in treating a vascular disorder. The embolic device can include a first coil segment, a second coil segment, and a mesh-screen segment disposed between the first coil segment and the second coil segment along a length of the embolic device.

In various embodiments, each of the first and second coil segments includes a helically wound wire. In some instances, the first and second coil segments each have a greater compliance than the mesh-screen segment. In some instances, the mesh-screen segment has a greater porosity than each of the first and second coil segments. When the mesh-screen segment is in a deployed configuration, the mesh-screen segment can be 60% to 80% porous.

In various embodiments, the mesh-screen segment includes two layers, which can have different thicknesses. In some cases, at least a portion of each of the two layers are disposed in different parallel planes. In some cases, at least a portion of each of the two layers are disposed in the same plane. In some instances, the two layers are fixed to each other. In other instances, the two layers are free to move with respect to each other. The two layers can be spaced apart from each other by a predetermined distance. Moreover, the mesh-screen segment can include through-thickness perforations. In certain instances, the mesh-screen segment further includes a first extension portion and a second extension portion adapted to be inserted into a lumen formed by the first coil segment and the second coil segment, respectively, to couple the mesh-screen segment to the first coil segment and the second coil segment. In some cases, different portions of the embolic device include different thermomechanical properties In general, in another aspect, embodiments of the invention feature a method for treating a vascular disorder of a patient. The method can include the step of delivering into the vascular disorder an embolic device including a coil segment and, coupled thereto, a mesh-screen segment, such that (i) the coil segment is disposed within a cavity formed by the vascular disorder and (ii) the mesh-screen segment is disposed across a neck of the vascular disorder.

In various embodiments, the vascular disorder is an aneurysm. In some instances, the delivering step includes releasing the device from a distal tip of a delivery pusher. In such instances, the method can further include advancing the delivery pusher through a microcatheter having a distal end disposed within the vascular disorder. The method can further include delivering a second embolic device into the vascular disorder without repositioning the microcatheter. In some instances, the initially-delivered embolic device includes an additional coil segment and the mesh-screen segment is disposed between the coil segment and the additional coil segment along a length of the embolic device. In some cases, the coil segment includes a helically wound wire. The coil segment can have a greater compliance than the mesh-screen segment. The mesh-screen segment can have a greater porosity than the coil segment. Upon delivery, the mesh-screen segment can be 60% to 80% porous.

In various embodiments, the mesh-screen segment includes two layers, which can have different thicknesses. In some cases, at least a portion of each of the two layers are disposed in different parallel planes. In some cases, at least a portion of each of the two layers are disposed in the same plane. In some instances, the two layers are fixed to each other. In other instances, the two layers are free to move with respect to each other. The two layers can be spaced apart from each other by a predetermined distance. The mesh-screen segment can include through-thickness perforations. In some cases, different portions of the embolic device include different thermomechanical properties In general, in yet another aspect, embodiments of the invention feature a method of manufacturing an embolic device. The method can include the steps of forming a first coil segment and a second coil segment, forming a mesh-screen segment, and coupling the mesh-screen segment between the first coil segment and the second coil segment along a length of the embolic device.

In various embodiments, the step of forming the first and second coil segments includes helically winding at least one wire. In some instances, the step of forming the mesh-screen segment includes using a subtractive manufacturing technique, e.g., a laser technique, a mechanical technique, a wet chemical technique, an electrochemical masking technique, a maskless electrochemical technique, etching, milling, photochemical machining, and/or photoelectrochemical machining. In some instances, the step of coupling the mesh-screen segment between the first coil segment and the second coil segment includes inserting a first extension portion and a second extension portion of the mesh-screen segment into a lumen formed by the first coil segment and the second coil segment, respectively. In some cases, the step of forming the first and second coil segments and/or the step of forming the mesh-screen segment includes forming different portions of the embolic device to have different thermomechanical properties.

These and other objects, along with advantages and features of the embodiments of the present invention herein disclosed, will become more apparent through reference to the following description, the accompanying drawings, and the claims. Furthermore, it is to be understood that the features of the various embodiments described herein are not mutually exclusive and can exist in various combinations and permutations.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings, in which:

FIG. 9 is an image of an exemplary attachment of an extension portion and a delivery pusher, according to one embodiment of the invention.

DESCRIPTION

Figure 1:
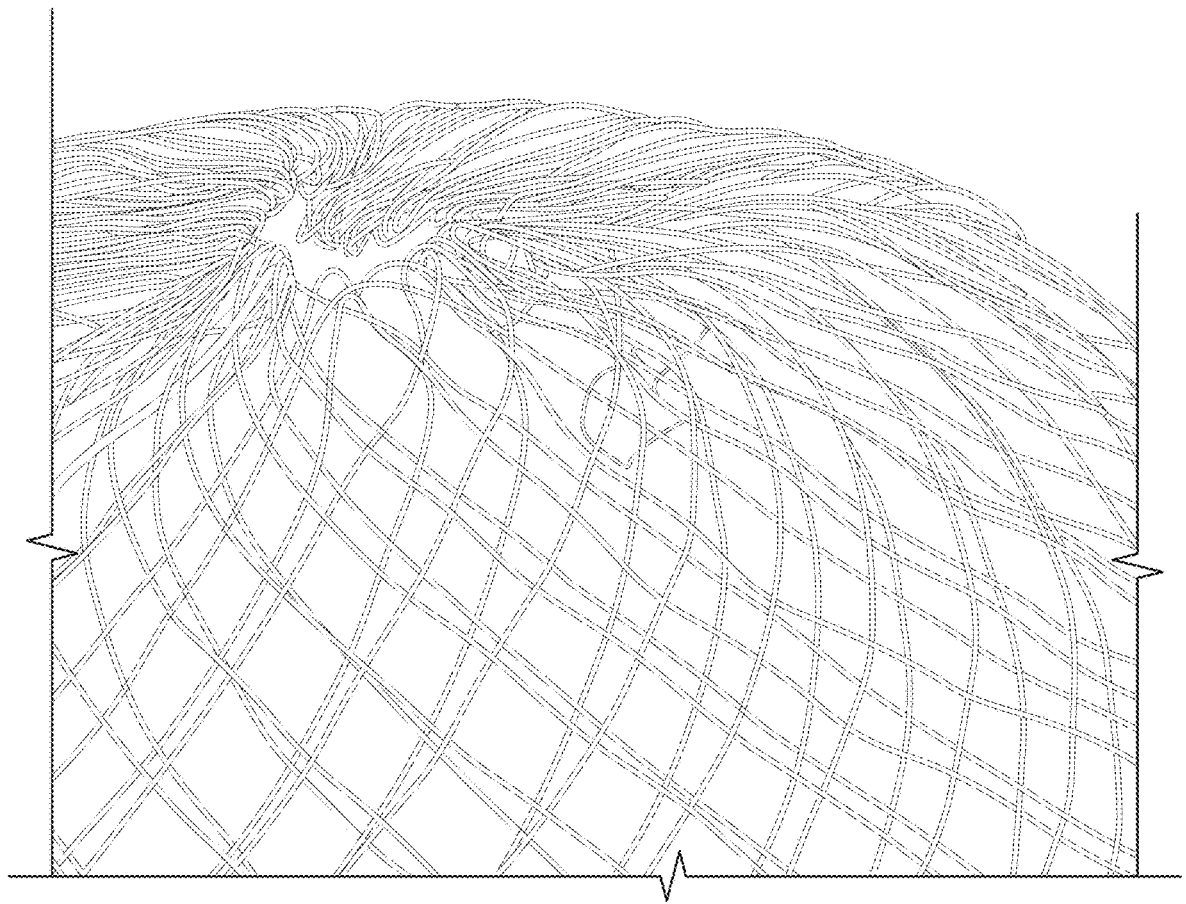
FIG. 1 is an image of an exemplary conventional embolic device formed from a braided wire.

Embodiments of the present invention are directed toward an improved design for an embolic device and methods of using and manufacturing the improved device. As mentioned above, porosity is a critical parameter for embolic devices because it determines how much fluid can pass through the embolic device into the aneurysm, which can directly impact how effective the embolic device is in treating the aneurysm. As shown in FIG. 1, in many conventional devices the desired porosity is achieved with a braid or mesh structure of overlapping wires that form pores 101 of a desired size. While this technique can be effective in generating desired porosity, the overlapping wires stiffen the device and reduce its compliance. Most conventional devices achieve the desired porosity over their entire length, which results in unnecessary and excessively high material density that significantly reduces the device's compliance.

The inventors developed a solution to this problem by recognizing and appreciating that the desired porosity is only necessary at limited discrete portions along the length of the device. In particular, the desired porosity need only be achieved at the portions of the device that interact with (and therefore affect) the blood flowing into the aneurysm. Typically, these portions are the portions of the device that, when the device is deployed, are located across the opening between the blood vessel and the cavity of the aneurysm (sometimes call the "neck" of the aneurysm). The inventors recognized that the remaining portions of the device, i.e., those that do not interact with or affect the blood flowing into the aneurysm, need not have the desired porosity. Examples of portions that do not interact with or affect the blood flowing into the aneurysm include portions of the device that, when the device is deployed, are located in the middle of the cavity or along the interior wall of the cavity. The inventors recognized and appreciated that the portions of the device that need not have the desired porosity can be configured differently than the porosity sections; for example, they can be configured to be significantly more compliant than the porosity sections, which can increase the overall compliance of the entire device.

Figure 2:
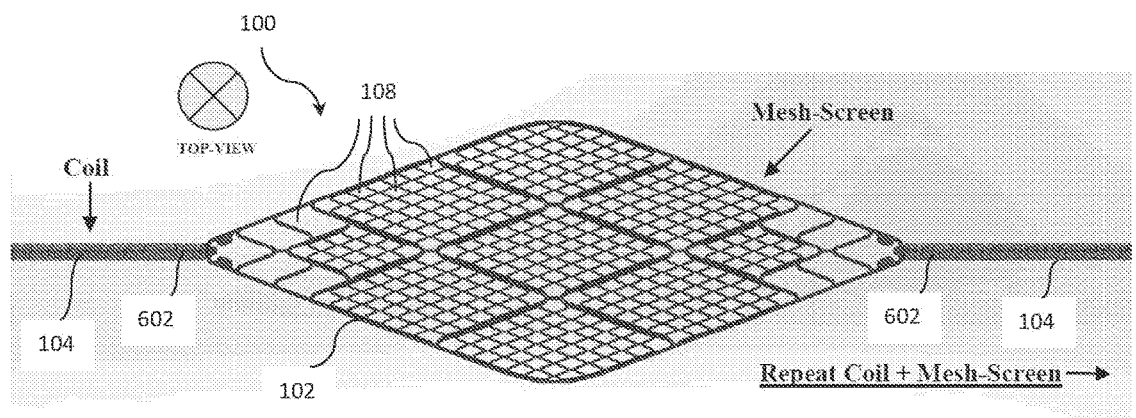
FIG. 2 is a top schematic view of an embolic device in a straightened out configuration, according to one embodiment of the invention.

A portion of an exemplary embodiment of the improved embolic device 100 of the present invention is shown in FIG. 2. The device 100 includes a porosity section 102 and compliance sections 104. Although FIG. 2 depicts one porosity section 102 and two compliance sections 104, in general the device 100 can include any number of porosity sections 102 (e.g., 1, 2, 3, etc.) and any number of compliance sections 104 (e.g., 1, 2, 3, etc.) as may be desirable for various applications. For example, in some embodiments the device 100 includes one porosity section 102 and one compliance section 104. As another example, the device 100 can include three porosity sections 102 and two compliance section 104. Many other examples are possible.

In various embodiments, the porosity section(s) 102 and the compliance section(s) 104 are arranged in a serially alternating fashion along the length of the device 100. As an example (and as shown in FIG. 2) the device 100 can include a compliance section 104, followed by a porosity section 102, followed by another compliance section 104, and optionally followed by another porosity section 102, etc. In other embodiments, the porosity section(s) 102 and compliance section(s) 104 can be arranged using any other arrangement. For example, multiple porosity sections 102 can be arranged adjacent to each other and/or multiple compliance sections 104 can be arranged adjacent to each other. In some cases, the arrangement of the porosity section(s) 102 and the compliance sections(s) 104 is constant (e.g., repetitive) along the entire length of the device 100. In other cases, the arrangement of the porosity section(s) 102 and the compliance section(s) 104 differs along the length of the device 100. For example, at certain locations the sections 102, 104 can be arranged in a serially alternating fashion, while at other locations the sections can be arranged with multiple porosity sections 102 and/or multiple compliance sections 104 adjacent to one another.

In various embodiments, the spacing between the segments of the device 100 is controlled to optimize the shape of the device 100 once it is delivered into the aneurysm. For example, in some cases the spacing between each porosity and/or compliance section can be uniform. In other cases, the spacing between each porosity and/or compliance section may vary along the length of the device 100. In general, the size and/or shape of the device 100 can be controlled and take any form to optimize the shape/size of the device 100 once it is delivered into the aneurysm.

In various embodiments, as shown in FIG. 2, the compliance sections 104 can be coil segments. Because the coil segment is an exemplary type of compliance section, both the coil segment and the compliance section are referred to in this application with the reference numeral 104. In some cases, the coil segment 104 is formed from a wound wire (e.g., a helically wound wire). A coiled structure is generally much more compliant than a braided structure and inclusion of these structures along the length of the device 100 can increase the overall compliance of the entire device 100. Although this specification often describes and depicts the compliance sections 104 as coiled structures, the compliance sections 104 can take other forms. In general, the compliance sections 104 can take any form that results in the sections 104 being more compliant than the porosity section 102. As one of many examples, the compliance sections 104 can be formed from braided wire and/or mesh segments, but with less material or otherwise configured such that they have greater compliance than the porosity section 102.

In various embodiments, the compliance sections 104 and the porosity section 102 can differ in properties other than or in addition to compliance. In general, the compliance section 104 and porosity section 102 can differ from each other with respect to any property and by any desirable amount. As one example, the compliance sections 104 and the porosity section 102 can have different thermomechanical properties from each other. An example material whose thermomechanical properties can be set to advantageous values is nitinol, but this can be done with other materials (e.g., most metals) as well. A non-exhaustive list of example thermomechanical properties that can differ between the compliance sections 104 and the porosity section 102 includes (i) strength, ductility, and/or toughness as a function of prior hot and/or cold working heat treatment, (ii) austenitic phase transformation temperature, and (iii) super-elasticity and shape memory properties (e.g., stress-strain behavior as a function of temperature and/or prior hot and/or cold working heat treatment). Many other examples of thermomechanical properties are also possible.

In other instances in which there are multiple compliance sections 104 and/or multiple porosity sections 102, different sections of the same type (e.g., different compliance sections 104 and/or different porosity sections 102) can have different properties from each other (e.g., thermomechanical properties). In still other instances, a single compliance section 104 and/or porosity section 102 can have different properties at different locations. As one example, a porosity section 102 can have a thermomechanical property having a first value near its center and a different value near its perimeter. One advantage of varying thermomechanical (or other) properties within the device 100 is that it can allow the device to be tuned to achieve desired deployment (or other performance) characteristics, e.g., by adjusting the phase transformation temperatures and/or expansion force characteristics at various locations of the device 100. In various embodiments, any two components (or locations thereof) of the device 100 can also have the same property as each other.

In various embodiments, the porosity section 102 itself has a novel and unique design that improves the function of the embolic device 100. In some cases, the improved porosity section 102 can be used with the compliance sections 104 (as described above), such that multiple features enhance the function of the device 100. In other cases, the entire device 100 can be formed from the improved porosity section 102, which can independently enhance the function of the device 100. In particular, in various embodiments, the porosity section 102 is formed from a novel and unique structure that features improved properties and characteristics over conventional braided/mesh wires, while still achieving the desired porosity. In various embodiments, the desired porosity can be in a range from about 50% to about 90% porous, in range from about 60% to about 80% porous, in a range from about 60% to about 70% porous, and in a range from about 70% to about 80% porous.

For example, the porosity section 102 can be a mesh-screen segment that is formed from at least one flat surface (e.g., a layer), as opposed to a cylindrical surface of a wire. Because the mesh-screen segment is an exemplary type of porosity section, both the mesh-screen segment and the porosity section are referred to in this application with the reference numeral 102. A structure formed from flat surface layers can be more flexible, crimp-resistant, and expandable than a structure formed from overlapping wires, while still achieving a desired porosity. In general, the mesh-screen segment 102 can be formed from any number of layers arranged/laminated in any desirable manner. For example, in the simplest case, the mesh-screen segment 102 is formed from a single layer. In other examples, the mesh-screen segment 102 is formed from multiple layers. In some cases, the various layers have different thicknesses and exist is different and/or overlapping parallel planes.

Figure 3:
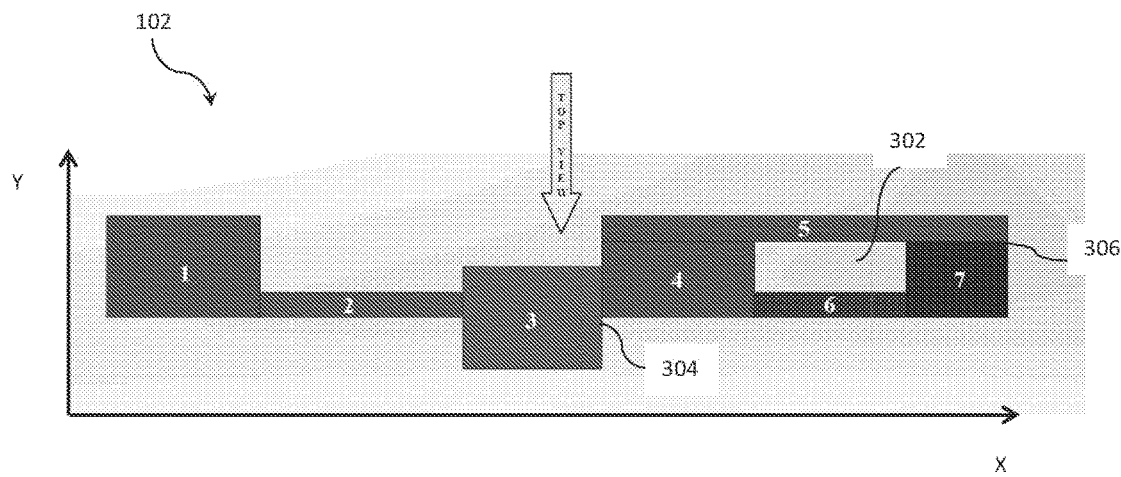
FIG. 3 is a side cross-sectional schematic view of a portion of an embolic device formed from multiple layers, according to one embodiment of the invention.

FIG. 3 is a side cross-sectional view of an exemplary, relatively complicated, layered structure. Each of elements 1 through 7 in FIG. 3 represents a different layer of a mesh-screen segment 102. As illustrated by layer 1 and layer 2, the layers can have different thicknesses (dimension along the y-axis). As illustrated by layer 3 and layer 4, at least a portion of different layers can exist in different parallel planes (e.g. the bottom portion of layer 3 and the top portion of layer 4 are in different parallel layers). Also illustrated by layer 3 and layer 4, at least a portion of different layers can exist in overlapping planes (e.g., the middle portion of both layer 3 and layer 4 overlap). As illustrated by layer 5 and layer 6, in some instances, certain layers do not overlap at all. Conversely, as illustrated by layer 4 and layer 7, certain layers can completely overlap (e.g., exist in the same plane over the entire thickness of one and/or both layers).

As illustrated by layer 5 and layer 6, the layers can have different widths (dimension along the x-axis). As illustrated by layer 1 and layer 4, the layers can have the same width. As illustrated by layer 5 and layer 6, in some instances, there can be a gap 302 between layers. The gap can exist in either the y-axis direction (shown in FIG. 3) or the x-axis direction. For example, gaps in the x-axis direction can be formed by through-thickness perforations formed in the mesh-screen segment 102. Exemplary through-thickness perforations 108 are shown in FIG. 2. When the device 100 is deployed within the aneurysm, fluid flows through the through-thickness perforations 108 to enter the aneurysm. Thus, the perforations 108 perform a similar function to the pores 101 formed in a conventional braided structure. For example, the size of the perforations 108 can determine the porosity of the mesh-screen segment 102, which in turn affects the amount of fluid that can traverse the mesh-screen segment 102 to enter the aneurysm. However, the perforations 108 are generally superior to the pores 101 of a braided structure because they can be configured to have a constant size (or a size with controlled variability, e.g., in embodiments in which the layers can move with respect to each other), which allows for a more consistent and predictable porosity to be achieved. In the conventional braided structure, the wires often move with respect to each other, which changes the pore size, making it harder to achieve a predictable porosity.

In general, the through-thickness perforations 108 can be formed in any shape or size so as to achieve a desired porosity. In some cases, the through-thickness perforations have a constant shape and size across the surface of the mesh-screen section 102. In other cases, the through-thickness perforations have different shapes and/or sizes at different locations across the surface of the mesh-screen section 102. In some instances, the through-thickness perforations affect other properties of the mesh-screen section 102, e.g., flexibility, expandability, crimp-resistance, etc.

As illustrated by all the layers in FIG. 3, the width of a layer can be less than the width of the entire mesh-screen section 102. In other instances, one or all of the layers can have a width that extends across the entire width of the mesh-screen section 102 (not shown in FIG. 3). In various embodiments, the relationships described above can exist between either adjacent or non-adjacent layers, in either the x-axis direction or the y-axis direction. Many other examples of relationships between layers are possible.

In various embodiments, the layers are joined at junctions 304 formed along the x-axis using any known technique. For example, the layers can be formed separately and joined using known attachment techniques (e.g., adhesives, welding, etc.). As another example, the layers can be formed from a single piece of material using subtractive manufacturing techniques (e.g., a laser technique, a mechanical technique, a wet chemical technique, an electrochemical masking technique, a maskless electrochemical technique, etching, milling, photochemical machining, and/or photoelectrochemical machining). In addition to junctions 304 formed between layers along the x-axis, junctions 306 can also be formed along the y-axis. In some cases, the layers are fixed at the junctions 306, e.g., using known joining techniques such as those described above. In some cases, the layers are free to move with respect to each other at the junctions 306. In certain instances, a single mesh-screen segment 102 can have some layers that are fixed to each other and other layers that are free to move with respect to each other.

Figure 4A:
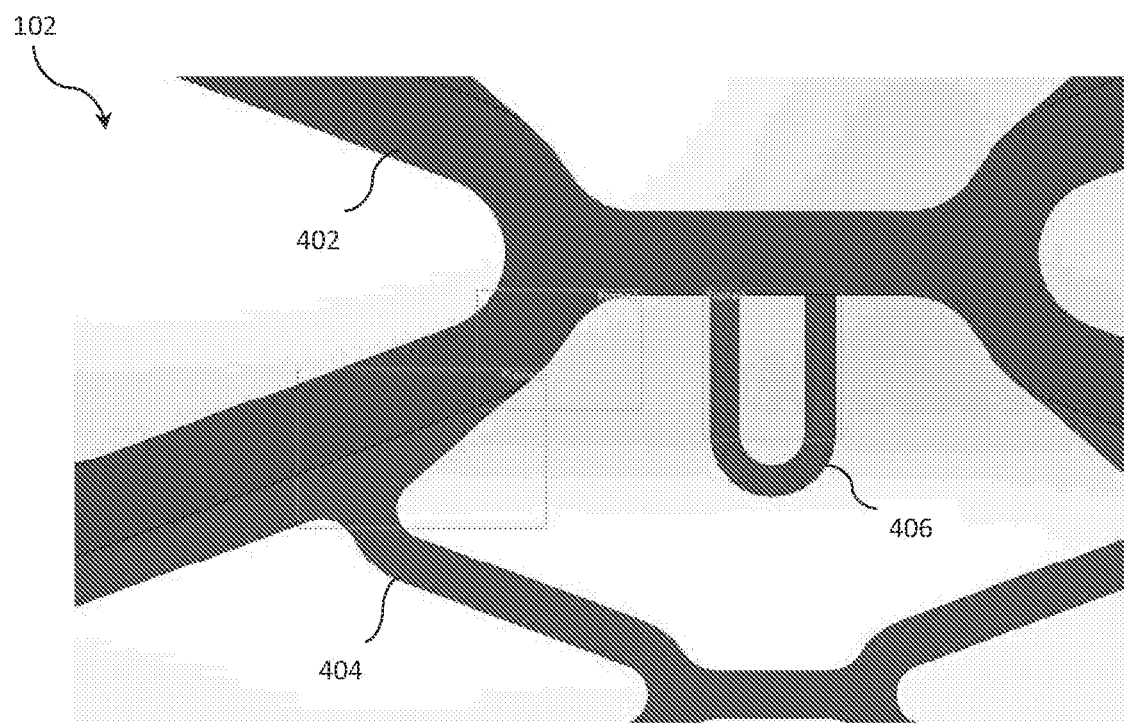
FIGS. 4A-4B are different schematic views of a portion of an embolic device formed from multiple layers, according to one embodiment of the invention.
Figure 4B:
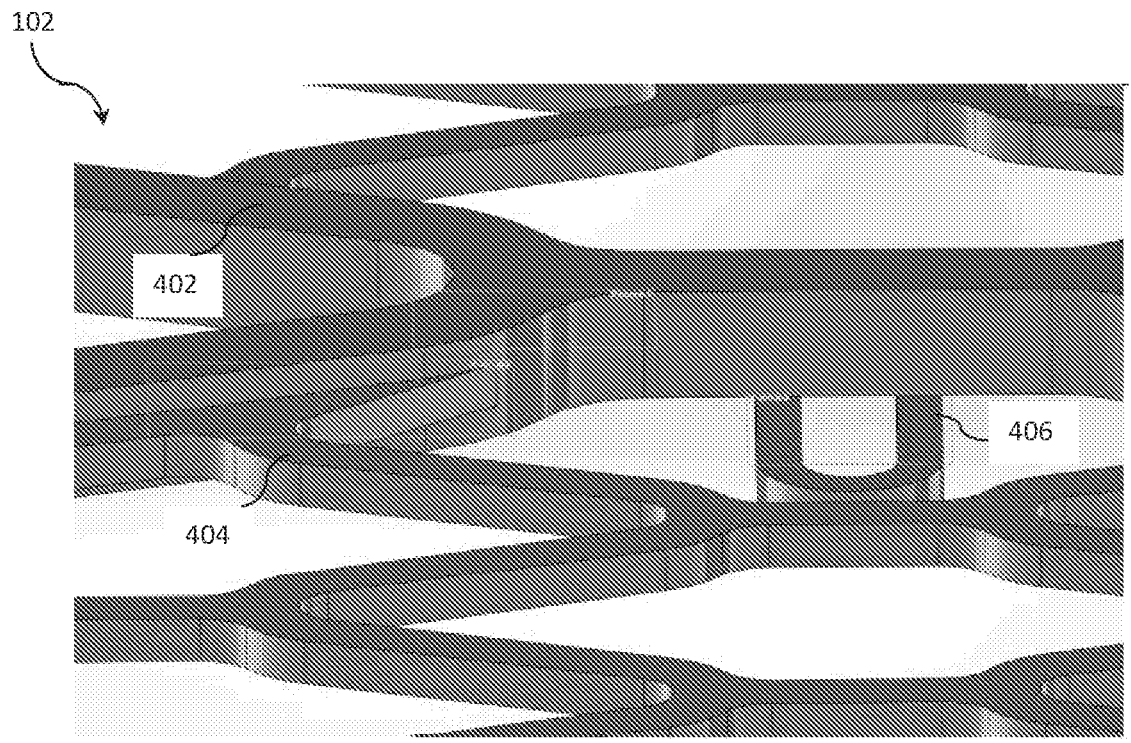

FIGS. 4A and 4B illustrate an exemplary configuration of a mesh-screen segment 102. FIG. 4A is a top view of the mesh-screen segment 102 showing layers 402, 404, and 406. FIG. 4B is a perspective view of the mesh-screen segment 102 showing that layers 402 and 404 have different thicknesses and that at least a portion of each of the layers 402, 404, and 406 exist in different planes.

Figure 5A:
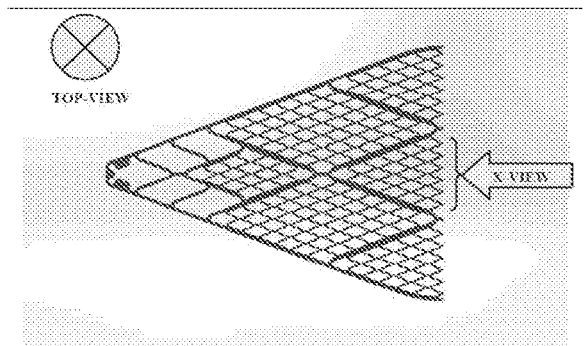
FIGS. 5A-5D illustrate various layer configurations of a portion of an embolic device, according to various embodiments of the invention.
Figure 5B:
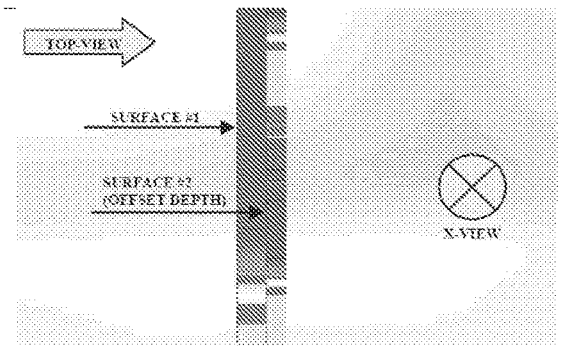
Figure 5C:
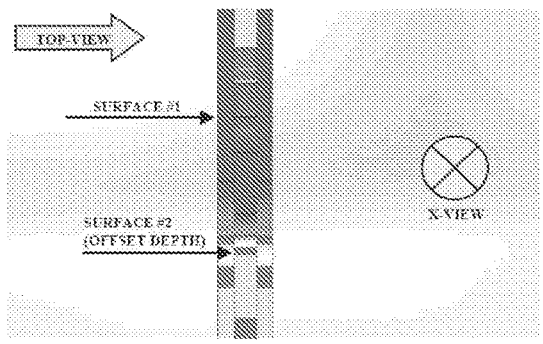
Figure 5D:
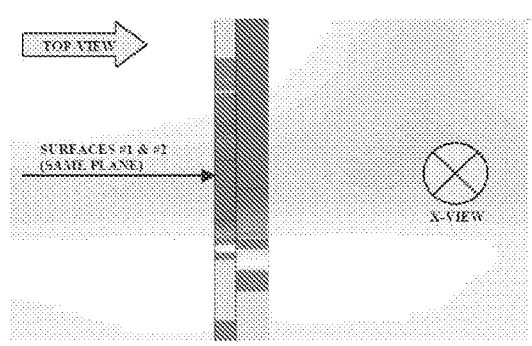

FIGS. 5A-5D provide further examples of various mesh-screen segment configurations. FIG. 5A indicates the point of view (i.e., the X-VIEW) from which each of FIGS. 5B-5D is depicted. FIG. 5B depicts a layered structure in which the leftmost edge of two surfaces (surface #1 and surface #2) are offset by a particular depth. FIG. 5C depicts a layered structure in which the leftmost edge of surface #1 and surface #2 are offset by a depth that is less than the offset depth shown in FIG. 5B. FIG. 5D depicts a layered structure in which the leftmost edge of surface #1 and surface #2 are not offset and exist in the same plane.

In general, the mesh-screen segment 102 can attach to adjacent sections using any technique that ensures proper attachment between the sections. For example, as shown in FIG. 2, in some embodiments the mesh-screen segment 102 includes at least one mesh-screen extension 602 that can be used to attach to adjacent sections. When the adjacent sections are coil segments 104, the mesh-screen extension 602 can extend into a lumen formed by the coil segment 104. The mesh-screen extension 602 can attach to the coil segment 104 using any suitable attachment or bonding scheme, e.g., mechanical mates, adhesive, welding, corresponding mating profiles, interlocking tabs, notch and grove arrangements, etc. In some cases, the mesh-screen extension 602 does not attach to the coil segment 104 directly, but rather, the coil segment 104 is held between two other structures that are attached by the mesh-screen extension 602 (e.g., two mesh-screen segments 102, a mesh-screen segment 102 and a delivery pusher, etc.) In some cases, the coil segment 104 can be held between two structures and attached directly to the mesh-screen extension 602. Similarly, the mesh-screen extension 602 can attach to a delivery pusher using any suitable attachment scheme. As one example shown in FIG. 9, the mesh-screen extension 602 forms a loop 902 that engages a wire 904 of a delivery pusher assembly. In some cases, the wire can be severed to release the mesh-screen extension 602 (and the device 100) from the delivery pusher. In other instances, the mesh-screen extension 602 attaches to a delivery pusher using corresponding mating profiles, interlocking tabs, notch and grove arrangements, adhesives, welding, etc.

In some embodiments, the mesh-screen extension 602 extends all the way through the coil segment 104 until it reaches another segment (e.g., another mesh-screen segment 102, a structure for attaching to a delivery pusher, etc.). In some instances, the mesh-screen extensions 602 extend over substantially the entire length of the device 100 (except for the mesh-screen segments 102 themselves) and form a core member of the device 100. In some cases, the mesh-screen extensions 602 ensure that the insertion forces applied from a delivery pusher are translated throughout the entire length of the device 100. This may be necessary, for example, if the coil segments 104 do not adequately translate the insertion force. In some cases, the mesh-screen extensions 602 can constrain the coil segments 104 and prevent undesirable stretching (or an undesirable amount of stretching) of the coil segments 104. As shown in FIG. 2, each mesh-screen segment 102 can have multiple mesh-screen extensions 602; for example, one mesh-screen extension 602 for each adjacent coil segment 104.

Figure 6:
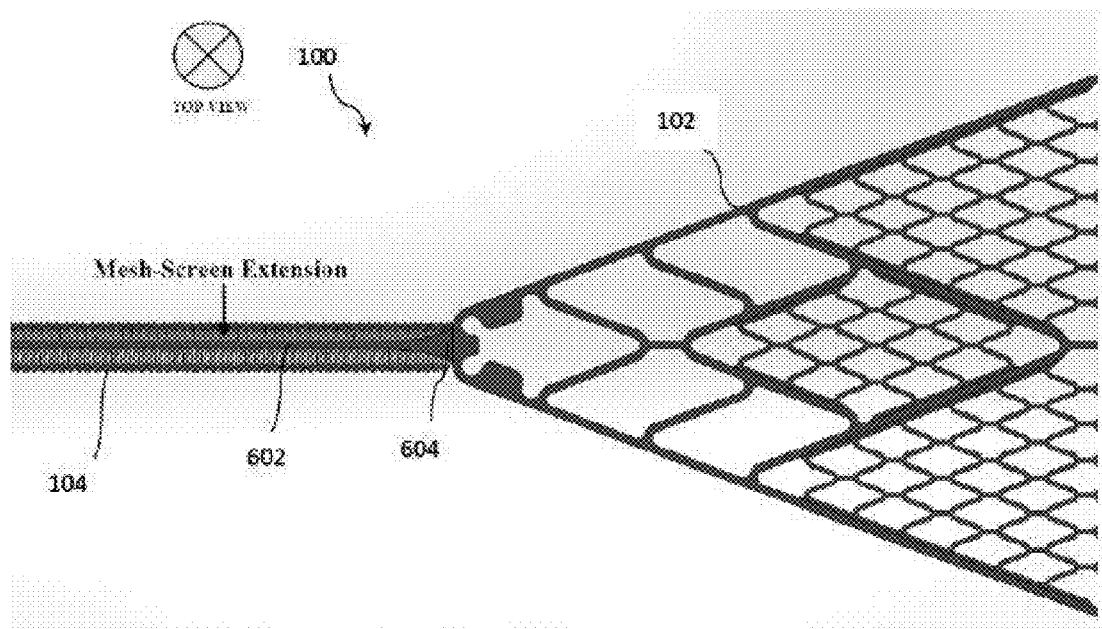
FIG. 6 is a top schematic view of an extension portion used to attach portions of an embolic device, according to one embodiment of the invention.

FIG. 6 is a close-up view of one of the mesh-screen extensions 602 shown in FIG. 2. As shown, the mesh-screen extension 602 can include a coupling feature 604 at its terminal end that can be used to attach to other segments and/or a delivery pusher. In some instances, the mesh-screen extension 602 is symmetric. In other instances, the mesh-screen extension 602 is non-symmetric. For example, the coupling feature 604 on either end of the mesh-screen extension 602 can be different (e.g., one coupling feature can be adapted to attach to a coil segment 104 and a different coupling feature can be adapted to attach to a delivery pusher).

In operation, the embolic device 100 may be introduced, delivered, positioned, and implanted within a vascular disorder using a microcatheter. The microcatheter can be a flexible, small diameter catheter having, for example, an inside diameter between 0.016 inches and 0.021 inches. The microcatheter may be introduced by an introducer sheath/guiding catheter combination placed in the femoral artery or groin area of a patient. In some instances, the microcatheter is guided into the vascular disorder with guidewires (e.g., long, torqueable proximal wire sections with more flexible distal wire sections designed to be advanced within tortuous vessels). Such a guidewire may be visible using fluoroscopy and may be used to first access the vascular disorder, thereby allowing the microcatheter to be advanced over it into the disorder.

Figure 7:
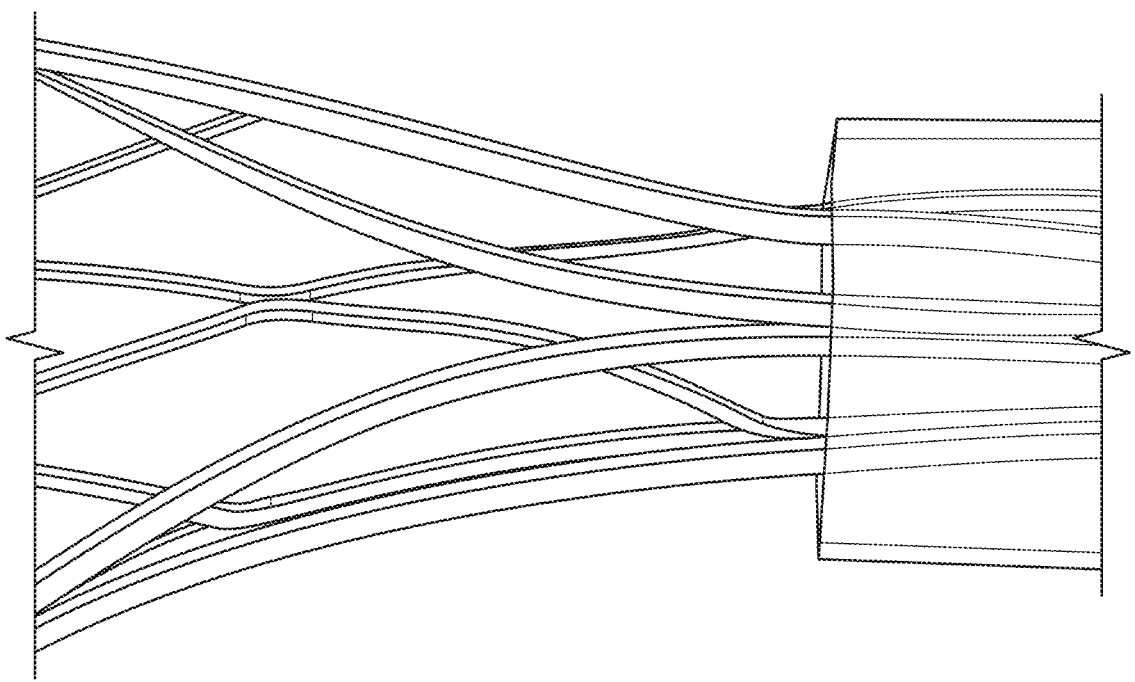
FIG. 7 is an image of an exemplary embolic device being inserted into a microcatheter, according to one embodiment of the invention.
Figure 8A:
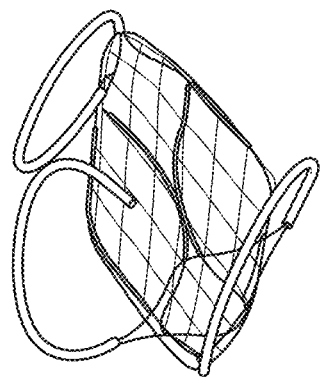
FIGS. 8A-8M are images of an exemplary embolic device in a deployed configuration and in various stages of deployment, according to various embodiments of the invention.
Figure 8B:
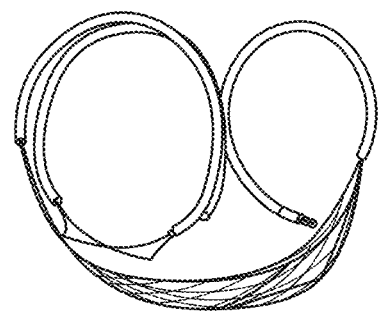
Figure 8C:
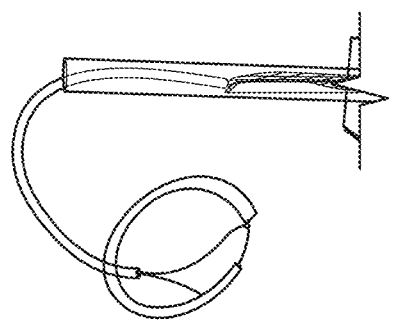
Figure 8D:
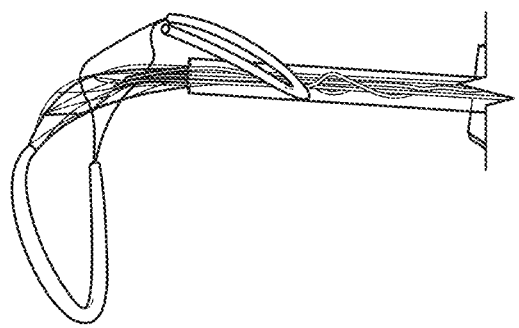
Figure 8E:
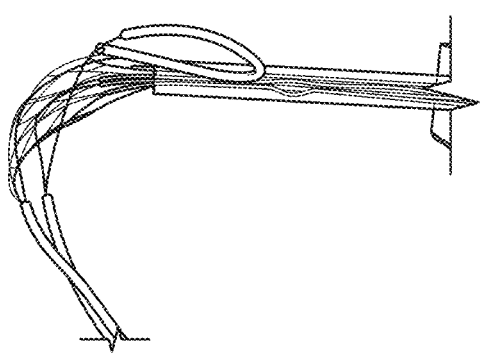
Figure 8F:
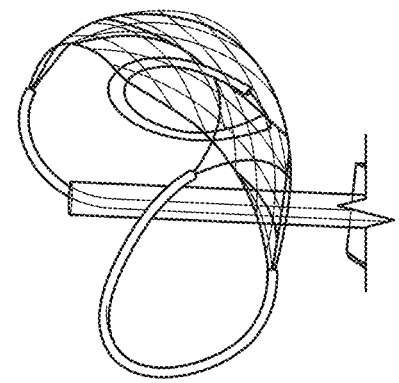
Figure 8G:
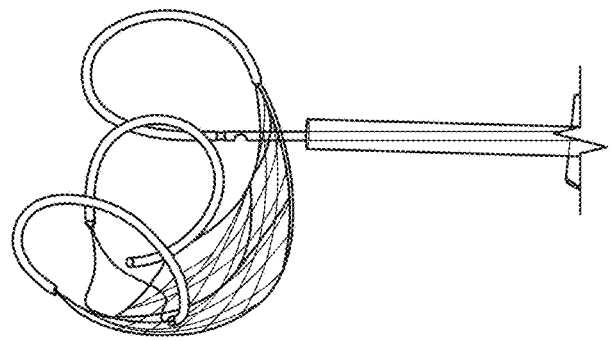
Figure 8H:
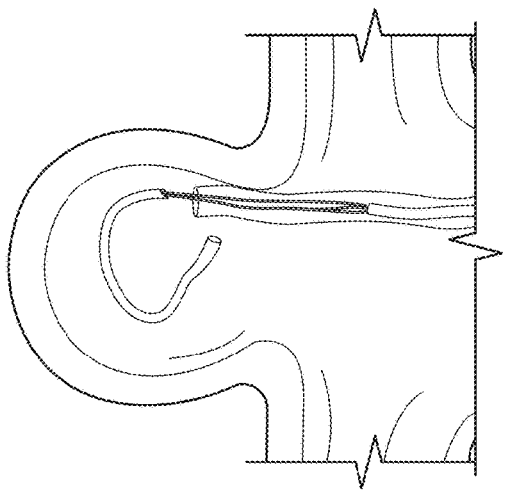
Figure 8I:
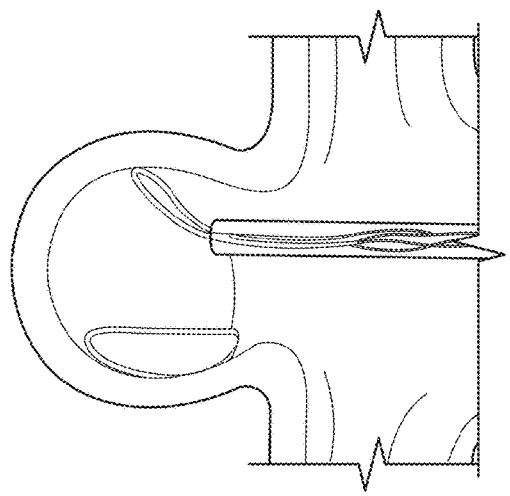
Figure 8J:
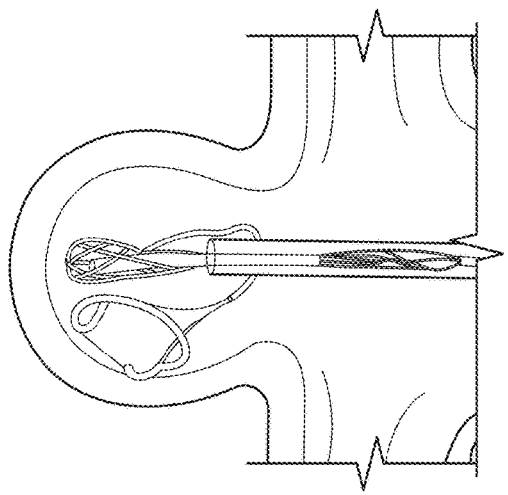
Figure 8K:
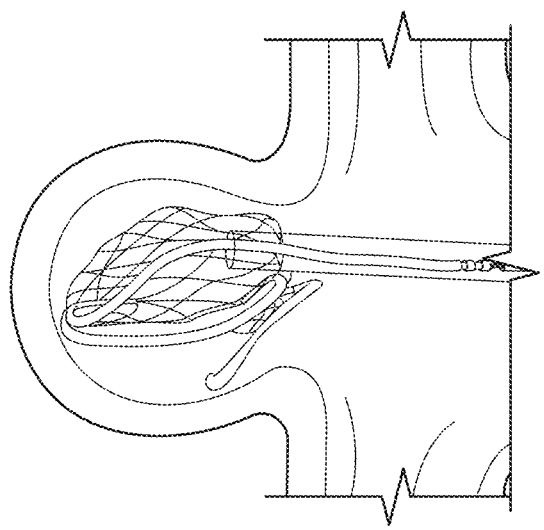
Figure 8L:
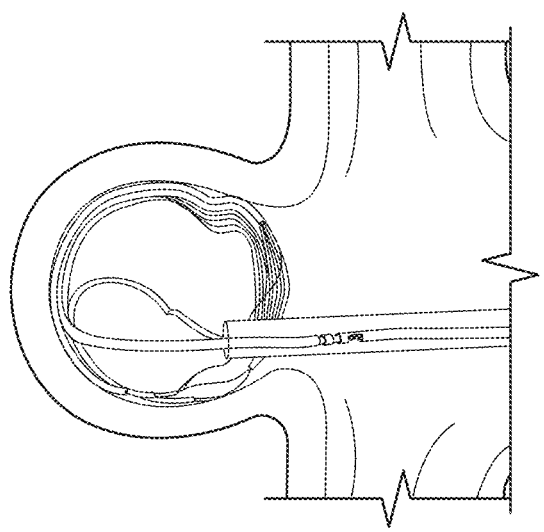
Figure 8M:
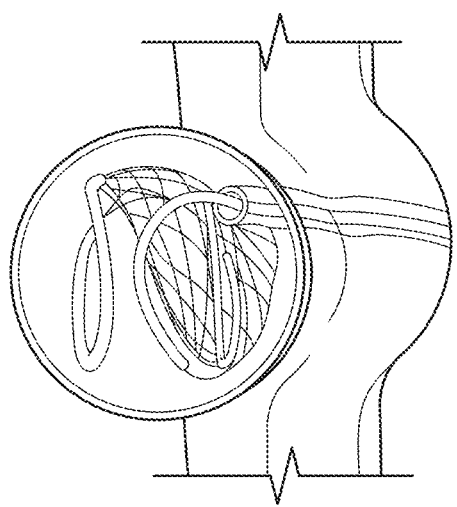

In some instances, once the tip of the microcatheter has accessed the vascular disorder, the guidewire is removed from the catheter lumen. The embolic device 100 may then be placed into the proximal open end of the microcatheter and advanced through the microcatheter with a delivery mechanism. While the embolic device 100 is disposed within the lumen of the microcatheter it may take a straightened out form. For example, the coil segments 104 can be straightened out to fit within the catheter lumen. In some cases, the mesh-screen section(s) 102 can be rolled, folded, or otherwise compressed so as to fit within the lumen of the microcatheter (see FIG. 7, as an example, with the microcatheter identified with reference numeral 702). A user (e.g., a physician) may advance and/or retract the embolic device 100 several times to obtain a desirable position of the embolic device 100 within the disorder. In some cases, a mesh-screen segment 102 can be guided and pushed by the adjacent coil segments 104. Once the embolic device 100 is satisfactorily positioned, it can be released into the disorder.

Upon release, the embolic device 100 can form a secondary shape. In some instances, the formation of a secondary shape upon deployment into the vascular disorder is caused by a shape-memory nature of the material (e.g., nitinol) used to form at least a portion of the embolic device 100 (e.g., the compliance sections 104). In general, the secondary shape can be any shape desirable to treat the aneurysm. For example, the shape can include a porosity section 102 disposed across a neck of the aneurysm and the compliance sections 104 arranged in the middle of the aneurysm cavity and/or along an interior wall of the aneurysm cavity, as may be desirable for treating the aneurysm. Exemplary images of the embolic device 100 formed into a secondary shape are shown in FIGS. 8A-8M. In images 8C-8M, the images depict the embolic device 100 being deployed from a microcatheter 702. In images 8H-8M, the images depict the embolic device 100 at various stages of deployment within a glass model aneurysm sac 802, which models the environment of an aneurysm within the body.

In various embodiments, the embolic device 100 is delivered in a more effective manner than conventional devices. For example, current techniques for delivering conventional braided devices typically have detachment zones that require the microcatheter to be placed directly at the neck of the aneurysm (i.e., not within the aneurysm cavity). Once the first device is released it blocks the neck of aneurysm and inhibits re-access to the cavity of the aneurysm, e.g., for the placement of additional devices/coils. This requires that the physician select a perfectly sized device that cannot be supplemented with additional devices, which can be challenging and often times not available.

Various embodiments of the present invention provide a solution to this problem. In particular, because the embolic device 100 does not include the high material density required to achieve the desired porosity along its entire length, the microcatheter can be placed directly within the aneurysm cavity for detaching the embolic device 100. After the first device 100 is deployed, the microcatheter can remain within the aneurysm cavity, such that additional devices/coils can be delivered without needing to remove or reposition the microcatheter. This can allow the physician to easily insert additional devices/coils which may be needed to "pack" the aneurysm and/or stabilize the embolic device 100. This functionality also alleviates the requirement that the embolic device 100 be perfectly sized, which can enable it to be used more often and to treat a greater number of aneurysms/vascular disorders.

In various embodiments, inclusion of the compliance sections 104 in the embolic device 100 results in the device 100 behaving more like a pure bare platinum coil than conventional braided devices. In general, the mechanical behavior and deployment of the embolic device 100 is much closer to that of a bare platinum coil than conventional braided devices. This can be advantageous because many physicians consider the feel of delivering a bare platinum coil to be familiar given traditional training and experience. Thus, the embolic devices 100 described in this application may be easier for physicians to adopt than conventional braided devices. In some embodiments, the embolic device 100 includes radiopaque sections (e.g., the coil segments 104) that can increase visibility of the embolic device 100 and improve safety during delivery, e.g., when exposed to fluoroscopic imaging. It is much more difficult to include radiopaque sections in conventional braided devices.

Other aspects of the invention generally relate to methods of manufacturing an embolic device 100. In general, the method can include forming a first coil segment and a second coil segment, forming a mesh-screen segment, and coupling the mesh-screen segment between the first coil segment and the second coil segment along a length of the embolic device. The components of the device can be manufactured using proven biocompatible materials and known manufacturing processes and techniques. For example, as described above, the coil segments 104 can be formed by helically winding wires and the mesh-screen segment 102 can be formed using standard joining techniques (e.g., adhesives, welding, etc.), subtractive manufacturing techniques, and/or combinations thereof. The mesh-screen segment 102 can be attached to the coil segments 104 using the mesh-screen extensions 602 or other techniques, as described above.

Having described certain embodiments of the invention, it will be apparent to those of ordinary skill in the art that other embodiments incorporating the concepts disclosed herein may be used without departing from the spirit and scope of the invention. Accordingly, the described embodiments are to be considered in all respects as only illustrative and not restrictive.

What is claimed is:

1. An embolic device for use in treating a vascular disorder, the embolic device comprising:
   a first compliant section;
   a second compliant section different than and separate from the first compliant section; and
   a mesh-screen segment formed from a non-braided structure comprising at least one flat surface layer,
   wherein the mesh-screen segment is disposed between the first compliant section and the second compliant section along a length of the embolic device, the first compliant section is connected to a first end of the mesh-screen segment and the second compliant section is connected to a second end of the mesh-screen segment,
   wherein the mesh-screen segment comprises a greater porosity than each of the first compliant section and the second compliant section.

2. The embolic device of claim 1, wherein the first and second compliant sections each comprise a coil comprising a helically wound wire.

3. The embolic device of claim 1, wherein the first and second compliant sections each comprise a greater compliance than the mesh-screen segment.

4. The embolic device of claim 1, wherein, when the mesh-screen segment is in a deployed configuration, the mesh-screen segment is 60% to 80% porous.

5. The embolic device of claim 1, wherein the mesh-screen segment comprises two layers.

6. The embolic device of claim 5, wherein the two layers have different thicknesses.

7. The embolic device of claim 5, wherein at least a portion of each of the two layers are disposed in different parallel planes.

8. The embolic device of claim 5, wherein at least a portion of each of the two layers are disposed in the same plane.

9. The embolic device of claim 5, wherein the two layers are fixed to each other.

10. The embolic device of claim 5, wherein the two layers are free to move with respect to each other.

11. The embolic device of claim 5, wherein the two layers are spaced apart from each other by a predetermined distance.

12. The embolic device of claim 1, wherein the mesh-screen segment comprises through-thickness perforations.

13. The embolic device of claim 1, wherein the mesh-screen segment further comprises a first extension portion and a second extension portion adapted to couple the mesh-screen segment to the first compliant section and the second compliant section, respectively.

14. The embolic device of claim 1, wherein different portions of the embolic device comprise different thermo-mechanical properties.

15. A method for treating a vascular disorder of a patient, the method comprising:
   delivering into the vascular disorder an embolic device comprising a first compliant section, a second compliant section different than and separate from the first compliant section, and a mesh-screen segment formed from a non-braided structure comprising at least one flat surface layer, wherein the mesh-screen segment is disposed between the first compliant section and the second compliant section along a length of the embolic device, wherein the first compliant section is connected to a first end of the mesh-screen segment and the second compliant section is connected to a second end of the mesh-screen segment, such that:
      the first and second compliant sections are disposed within a cavity formed by the vascular disorder, and
      the mesh-screen segment is disposed across a neck of the vascular disorder.

16. The method of claim 15, wherein the vascular disorder comprises an aneurysm.

17. The method of claim 15, wherein the delivering step comprises releasing the device from a distal tip of a delivery pusher.

18. The method of claim 17, further comprising advancing the delivery pusher through a microcatheter having a distal end disposed within the vascular disorder.

19. The method of claim 18, further comprising delivering a second embolic device into the vascular disorder without repositioning the microcatheter.

20. The method of claim 15, wherein the first and second compliant sections each comprise a coil comprising a helically wound wire.

* * * * *